United States Patent [19]

Shaltiel et al.

[11] Patent Number: 5,215,888
[45] Date of Patent: Jun. 1, 1993

[54] KIT FOR ASSAYING THE CELLULAR INTEGRITY OF BLOOD PLATELETS

[75] Inventors: Shmuel Shaltiel; Beatriz Grodzicki, both of Rehovot; Daniel Chain, Jerusalem, all of Israel

[73] Assignee: Yeda Research and Development Co. Ltd., Rehovot, Israel

[21] Appl. No.: 456,792

[22] Filed: Dec. 27, 1989

[30] Foreign Application Priority Data

Dec. 29, 1988 [IL] Israel .................................. 088831

[51] Int. Cl.⁵ .......................... C12Q 1/00; C12Q 1/56; C12Q 1/48
[52] U.S. Cl. ..................................... 435/15; 435/975; 435/13; 435/810; 435/4
[58] Field of Search ...................... 435/4, 15, 810, 194, 435/975

[56] References Cited

U.S. PATENT DOCUMENTS

| | | | |
|---|---|---|---|
| 4,594,319 | 6/1986 | Sharma et al. | 435/7 |
| 4,894,440 | 1/1990 | Rosenberg | 530/351 |
| 4,923,802 | 5/1990 | Gallis | 435/15 |
| 4,931,002 | 6/1990 | Kornecki et al. | 424/529 |
| 5,049,659 | 9/1991 | Cantor et al. | 530/351 |
| 5,084,565 | 1/1992 | Parodos et al. | 536/27 |

FOREIGN PATENT DOCUMENTS

0271810A3  6/1988  European Pat. Off. .

OTHER PUBLICATIONS

Korc-Grodzicki, B. et al (1988), "Platelet stimulation releses a cAMP-dependent protein kinase that specifically phosphorylates a plasma protein", *Proc. Natl. Acad. Sci. U.S.A.*, vol. 85, pp. 7541-7545.

Suzuki, S. et al (1984), "Domain structure of vitronectin", *The Journal of Biological Chemistry*, vol. 259, pp. 15307-15314.

Korc-Grodzicki, B. et al (1988), "Vitronectin is phosphorylated by a cAMP-dependent protein kinase released by activation of human platelets with thrombin", *Biochemical and Biophysical Research Communications*, vol. 157, No. 3, pp. 1131-1138.

Primary Examiner—David M. Naff
Assistant Examiner—Mike Meller
Attorney, Agent, or Firm—Browdy and Neimark

[57] ABSTRACT

There is provided a kit or reagent for assaying the cellular integrity (intactness) of blood platelets comprising means for determining the quantity of PKA released by a number of platelets into a certain volume of plasma. The assay is based on determining cAMP-dependent phosphorylation of vitronectin (protein S) in plasma using radioactively labelled [$\gamma^{32}P$]ATP as phosphate donor. The assay can be based on the specific inhibition of the phosphorylation in blood fluid by protein kinase inhibitors. The invention further relates to pharmaceutical compositions for the treatment of pathological conditions associated with impaired platelet function in humans, which comprises administering to a person in need thereof a physiologically active quantity of a PKA inhibitor adapted to decrease or prevent vitronectin phosphorylation. The inhibitor can be synthetic or genetically engineered peptide.

14 Claims, 3 Drawing Sheets

FIG. 4

| M.W. kD. | αV | | αF | | αP | |
|---|---|---|---|---|---|---|
| 94 — | | ● | | ■ | | ▬ |
| 67 — | | | | | | |
| 43 — | | | | | | |
| 30 — | | | | | | |
| | S | P | S | P | S | P |

FIG. 6

| A | B | C | D | E | F | G | H | kD |
|---|---|---|---|---|---|---|---|---|
| | | | | | | | | — 94 |
| ▬ | ▬ | ▬ | ▬ | ▬ | ▬ | ▬ | ▬ | — 67 |
| | | | | | | | | — 43 |
| | | | | | | | | — 30 |
| 6.0 | | 6.5 | | 7.0 | | 7.5 | | pH |
| − | + | − | + | − | + | − | + | Heparin |

KIT FOR ASSAYING THE CELLULAR INTEGRITY OF BLOOD PLATELETS

FIELD OF THE INVENTION

The invention relates to a kit or reagent for assaying the cellular integrity (intactness) of blood platelets which comprises means for determining the quantity of cAMP-dependent protein kinase (PKA) released by a number of stimulated platelets into a certain volume of plasma. More specifically, it relates to a kit or reagent wherein cAMP-dependent phosphorylation of vitronectin (protein S) is determined in plasma using radioactively labelled ATP as phosphate donor, comprising means for determining the radioactivity of the PKA-phosphorylated vitronectin.

According to a preferred embodiment, the specific inhibition of the phosphorylation in blood fluid by protein kinase inhibitors is determined. There is also provided a radioimmunoassay for assessing the cellular integrity of blood platelets, which comprises means for monitoring the release of PKA in plasma by means of anti-PKA, anti-phosphovitronectin or anti-vitronectin antibodies.

A specific embodiment relates to a kit or reagent for assaying the biological functionality of isolated blood platelets which comprises means for determining their ability to release PKA when stimulated with a physiological platelet agonist (thrombin, collagen, ADP, etc.) wherein the determination of the released PKA is effected as described above. Furthermore, the invention relates to a pharmaceutical composition for the treatment of pathological conditions associated with impaired platelet function in humans, which comprises administering to such a person in need thereof a physiologically active quantity of a PKA inhibitor adapted to decrease or prevent vitronectin phosphorylation. Preferably, the inhibitor is a synthetic or genetically engineered peptide containing any of the sequences

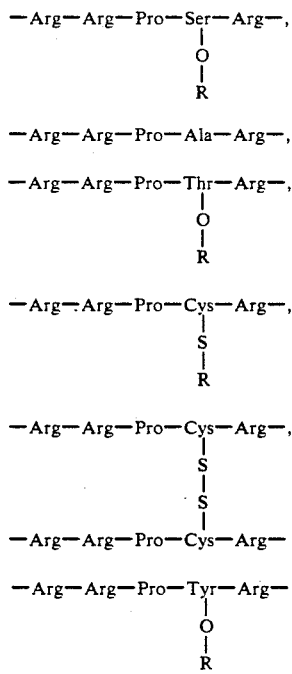

wherein R is a protecting group or hydrogen. In the above, one, two or all three Arg residues can be replaced by Lys and these can be used as a peptide which contains a sequence analogous to Arg-Arg-Pro-Ser-Arg.

BACKGROUND OF THE INVENTION cAMP-mediated protein phosphorylation plays a key role in the intracellular response of eukaryotic cells to hormonal signals (1,2). In the laboratory of the present inventors, there has recently been suggested a possible extracellular function for PKA in rabbit blood (3). It was based on the observation that thrombin-activation of rabbit platelets causes them to release PKA (alongside with its co-substrate ATP (4)) which then specifically phosphorylates a plasma protein (M, 135000) in a cAMP-dependent process (3).

In view of the implications such a phosphorylation may have in hemostasis and thrombosis, there was a need to determine whether or not thrombin similarly releases PKA from human platelets and to identify the human plasma protein, if any, which constitutes the PKA target substrate.

SUMMARY OF THE INVENTION

The present invention is based on the inventors' findings which show that upon stimulation of human platelets with a physiological platelet-stimulant (such as thrombin), they release PKA into the blood fluid, and that in human plasma there is a specific target substrate (p75) for this kinase. This target substrate has been shown to be vitronectin, a protein which has been implicated in cell adhesion, complement function and blood clotting (6–11). A description of these findings appears in publication 5, the entire contents of which are hereby incorporated by reference.

The present invention relates to a kit or reagent for assaying the cellular integrity (intactness) of blood platelets which comprises means for determining the quantity of PKA released by a number of stimulated platelets into a certain volume of plasma. More specifically, it relates to a kit or reagent wherein cAMP-dependent phosphorylation of vitronectin (protein S) is determined in plasma using radioactively labelled ATP as phosphate donor, comprising means for determining the radioactivity of the PKA- phosphorylated vitronectin.

According to a preferred embodiment, the specific inhibition of the phosphorylation in blood fluid by protein kinase inhibitors is determined. There is also provided a radioimmunoassay for assessing the cellular integrity of blood platelets, which comprises means for monitoring the release of PKA in plasma by means of anti-PKA, anti-phosphovitronectin or anti-vitronectin antibodies.

A specific embodiment relates to a kit or reagent for assaying the biological functionality of isolated blood platelets which comprises means for determining their ability to release PKA when stimulated with a physiological platelet agonist (thrombin, collagen, ADP, etc.) wherein the determination of the released PKA is effected as described above. Furthermore, the invention relates to a pharmaceutical composition for the treatment of pathological conditions associated with impaired platelet function in humans, which comprises administering to such a person in need thereof a physiologically active quantity of a PKA inhibitor adapted to decrease or prevent vitronectin phosphorylation. Preferably, the inhibitor is a synthetic or genetically engineered peptide containing any of the sequences

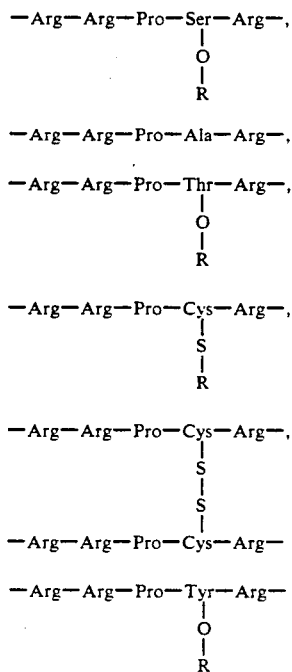

wherein R is group or hydrogen. In the above, one, two or all three of the Arg residues can be replaced by Lys and these can be used as a peptide which contains a sequence analogous to Arg-Arg-Pro-Ser-Arg.

Furthermore, the invention relates to a method for determining the integrity and/or biological functionality of blood platelets which comprises determining the quantity of PKA released by such platelets into plasma and evaluating the quantity released. It further relates to a method for the determination of the cellular integrity and/or biological functionality of blood platelets based on the determination of cAMP-dependent phosphorylation of vitronectin in plasma and/or the inhibition of such phosphorylation with radioactively labelled [$\gamma^{32}$P]ATP as phosphate donor, and determining the degree of phosphorylation, and/or its prevention which is indicative of the quantity of PKA released by the platelets into the plasma.

BRIEF DESCRIPTION OF THE DRAWINGS

FIG. 4 shows the results of polyacrylamide gel electrophoresis and autoradiography of the product of immunoreaction of the p75 peak fraction of FIG. 3 with antibodies against vitronectin, fibrinogen and plasminogen.

FIG. 6 shows results of polyacrylamide gel electrophoresis and autoradiography of the phosphorylation of vitronectin at various pH's in the presence or absence of added heparin.

DETAILED DESCRIPTION OF PREFERRED EMBODIMENTS

Figure 1:
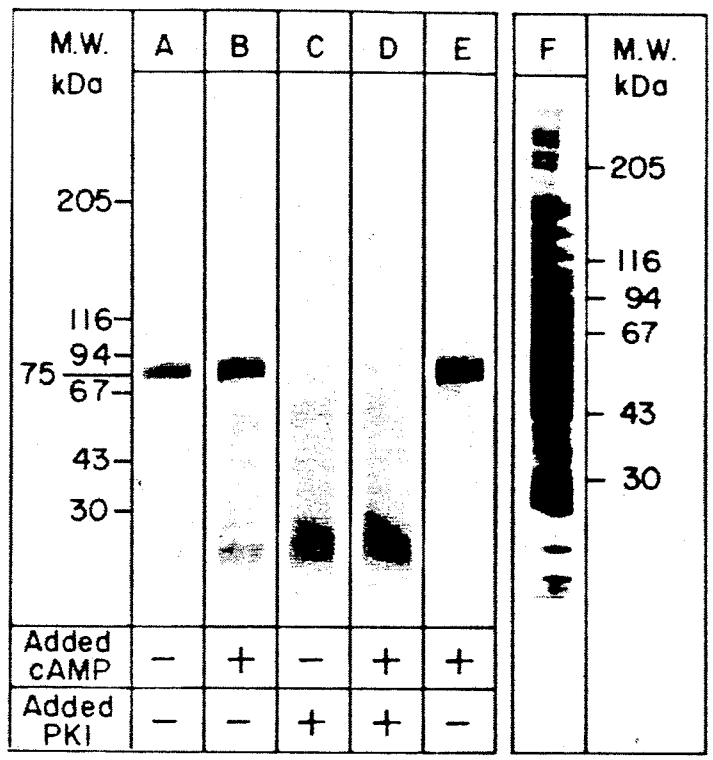
FIG. 1 shows the results of gel electrophoresis and autoradiography on variously treated serum samples after endogenous phosphorylation.

Activation of freshly isolated human blood platelets with physiological stimulants (e.g., thrombin) causes them to release a cAMP-dependent protein kinase which specifically phosphorylates one plasma protein ($M_r$ 75000). This protein has now been immunochemically and biochemically identified as vitronectin (also known as S protein), which has previously been implicated in blood clotting, complement function and cell adhesion. These findings form the basis for the present invention which comprises (a) the development of diagnostic kits and reagents for assessing the integrity and physiological functionality of blood platelets as well as to a method for carrying out such determination; and (b) the design of pharmaceutically active drugs for modulation of vitronectin function and thus controlling pathological conditions involving platelet malfunction (12).

The assessment of the platelet integrity and functionality is based on the measurement of PKA released upon the physiological stimulation of such platelets into plasma or into any other medium. The determination is preferably carried out using the cAMP-dependent phosphorylation of vitronectin (S protein) with radioactively labelled ATP ([$\gamma^{32}$P]ATP) as phosphate donor. The inhibition of phosphorylation by specific protein kinase peptide inhibitors can also be used in such assay.

The method of assessing platelet integrity and functionality may take place using the endogenous phosphorylation, i.e., the endogenous release of PKA by the platelets, using radioactively labelled ATP as phosphate donor, or the process may take place in the presence of a physiological platelet agonist. Such agonists known to stimulate platelets are known to those of ordinary skill in the art and any such agonist may be used as long as it is capable of stimulating the release of PKA in healthy platelets. Non-limiting examples include thrombin, collagen and ADP. Furthermore, while radioactive marking of the phosphate with [$\gamma^{32}$P]ATP is specifically exemplified as the preferred manner of determining the degree of phosphorylation of vitronectin, it should be understood that any manner of marking the phosphate donor can be used. The present invention does not specifically lie in the manner of determining how much vitronectin is phosphorylated but in the concept of looking for such a factor as a means of determining how much PKA has been released by the platelets and thus assessing platelet integrity and functionality. The measurement of the amount of marked phosphate, such as measurement of the amount of radioactivity in the preferred embodiment, by the vitronectin will provide a measured parameter which is directly related to the amount of PKA being released by the platelets. Comparison with such results with the measured parameters attained using normal healthy platelets will provide an indication of the integrity and functionality of the platelets in the test subjects.

It has also been discovered that the presence of heparin will cause an increase in the amount of phosphorylation of vitronectin which takes place. Accordingly, the present invention also comprehends the addition of heparin to the platelet sample being assessed. Besides heparin, related compounds such as heparin sulfate or any other related compound which has similar physiological activity of heparin, particularly such compounds which bind to the heparin binding domain of vitronectin (15) may be used.

Another method of determining the amount of PKA being released by the platelets in the sample involves the use of an immunoassay technique using anti-PKA, anti-vitronectin and/or anti-phosphovitronectin antibodies. Such antibodies may be monoclonal or polyclonal and may be produced by any of the techniques well known in the art. In this regard the entire contents of Harlow and Lane, "Antibodies: A Laboratory Manual", Cold Spring Harbor Laboratory, 1988, is hereby incorporated by reference. Such antibodies may be labelled in any known manner, such as by radiolabelling, enzyme labelling, fluorescent labelling, etc., and the assay may be carried out using any known immunoassay technique, such as antibody capture assays, two-antibody sandwich assays, antigen capture assays, etc. (see Harlow and Lane, supra). For example, radiolabelled anti-PKA antibodies may be used to bind to PKA and thereby determine the quantity of PKA being released by the platelets.

The reagents necessary for conducting the assays discussed above may be provided in the form of a kit. Such a kit may contain $[\gamma^{32}P]ATP$ in appropriate solution for use in performing the assay along with appropriate titre plates, tubes, or other containers in which the reaction is to take place and instructions for conducting the assay, all appropriately packaged. The kit may also contain vials of heparin and platelet agonist. When the assay is an immunoassay, the kit will include the appropriately labelled antibodies preferably along with appropriate titre plates or containers for conducting the reaction and instructions, all appropriately packaged.

The present inventors have discovered that the site of phosphorylation of vitronectin by PKA released from stimulation of platelets by their physiological stimulants comprises the octapeptide sequence -Ser-Arg-Arg-Pro-Ser-Arg-Ala-Thr-. A synthetic octapeptide of such sequence has been shown to compete with (inhibit) the phosphorylation of vitronectin by PKA. The smallest portion of this sequence which will competitively inhibit phosphorylation of vitronectin by PKA is -Arg-Arg-Pro-Ser-Arg-. This sequence can be modified and still retain its inhibiting ability. For example, the Ser can be replaced by Thr, Ala, Cys or Tyr. Furthermore, one, two or all three of the Arg peptides can be replaced by Lys. The hydroxide groups of the Ser, Thr or Tyr groups or the —SH group of the Cys may be in their free form or in a protected form. Thus, the H in the —OH or —SH groups of these peptides may be replaced by a protecting group which will prevent any phosphorylation of the peptide but will not affect the ability of the oligopeptide to bind to PKA. Non-limiting examples of such protecting groups include methyl acetyl, phenyl, benzoyl, phosphate, thiophosphate, and sulfate. Those of ordinary skill in the art can readily determine what groups will prevent phosphorylation of the peptide but will not otherwise effect the ability of the oligopeptide to bind to PKA and thus compete with the PKA binding site on vitronectin. If in doubt, a routine in vitro experiment will determine whether or not a peptide with such a protecting group will compete with and thus inhibit binding to vitronectin and whether or not the peptide becomes phosphorylated by the PKA.

Any of the above-described oligopeptide PKA inhibitors can be used clinically as the active ingredient of a pharmaceutical composition for the treatment of pathological conditions associated with impaired platelet function, such as platelet disorders (12). As such PKA inhibitors serve to modulate vitronectin function, they can be used clinically when such modulation in vivo is desired. Additionally, such oligopeptides have a valuable utility as a tool used in the study of the specific physiological roles of vitronectin and phosphovitronectin.

The maximum size of the oligopeptide containing the pentapeptide sequence described above is not critical as long as it retains the PKA inhibiting activity of the pentapeptide and is not otherwise toxic.

To form a pharmaceutical composition, the active principle may be formulated with any pharmaceutically acceptable excipient so as to place it into appropriate administratable form.

Thus, the present invention further comprehends pharmaceutical compositions for the modulation and thus the treatment of pathological conditions associated with impaired platelet function in humans, which composition comprises a physiologically active quantity of an alternative PKA substrate or a peptide inhibitor adapted and optimalized to decrease or prevent vitronectin phosphorylation.

The pharmaceutical compositions of the invention are preferably administered by injection or infusion. The dosage depends on the disorder, and will be determined from case to case by the attending physician and will generally be in the range of from about 10 mg to about 500 mg per day per adult, preferably divided into a number of doses.

The pharmaceutical compositions of choice comprise as active ingredient a peptide (natural, synthetic or genetically engineered) which contains one of the sequences:

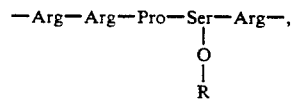

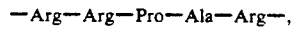

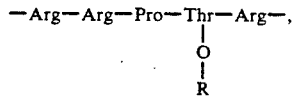

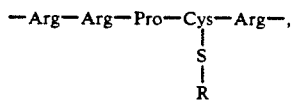

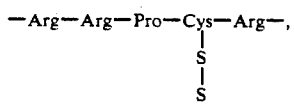

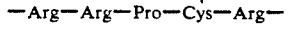

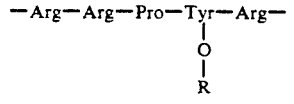

wherein R is a protecting group, or hydrogen or a physiological equivalent thereof. The —OR groups shown as being attached to a Ser, Thr or Tyr group and the —SR group shown as being attached to a Cys group, actually are the endogenous —OH or —SH moieties of the peptides shown broken out for emphasis. Thus, when the R group is H the peptides are unchanged and when R is a protecting group the protecting group replaces the H of the endogenous —OH or —SH groups of the peptides. In the above, one, two or all three Arg residues can be replaced by Lys and these can be used as a peptide which contains a sequence analogous to Arg-Arg-Pro-Ser-Arg.

Other and further aspects of the invention will become apparent hereinafter.

EXAMPLE I

Fresh human blood obtained by venipuncture of healthy individuals, who had fasted overnight and who had ingested no drugs for at least two weeks prior to blood withdrawal, was allowed to clot in a glass tube and the resulting serum was subjected to endogenous phosphorylation with [$\gamma^{32}$P]ATP and Mg$^{++}$. One protein band ($M_r$ 75000) became phosphorylated (FIG. 1, lane A). This phosphorylation was enhanced by added cAMP (FIG. 1, lane B) and prevented by the Walsh-Krebs (13) specific PKA inhibitor (PKI) (FIG. 1, lanes C and D) indicating that it was catalyzed by PKA.

As seen in FIG. 1, the endogenous phosphorylation in human serum was specific: one protein was singled out from the large repertoire of serum proteins (FIG. 1, compare lanes A and B with lane E) and became phosphorylated in a cAMP-dependent process. The protein phosphorylated in human blood had a molecular weight of 75000 (p75), and was shown to be vitronectin (v.i) (5).

EXAMPLE II

Figure 2:
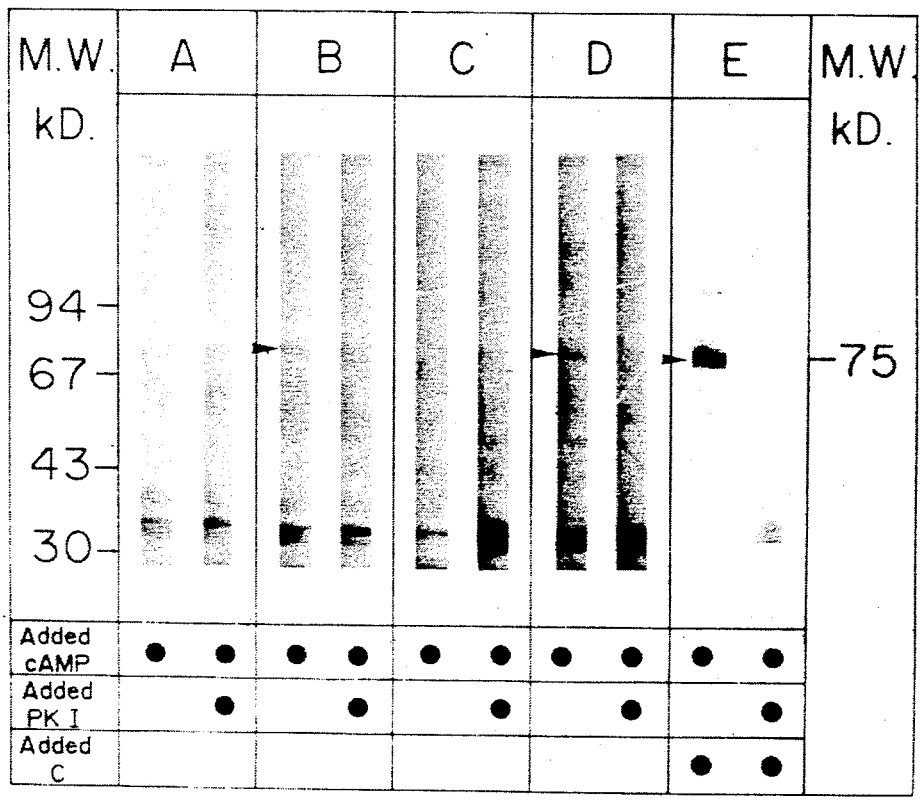
FIG. 2 shows the results of gel electrophoresis and autoradiography of variously treated serum samples after adding cAMP.

Fresh human blood (see Example I) was used to prepare platelet-containing plasma, platelet-free plasma and gel-filtered ("washed") platelets, taking measures to avoid platelet breakage. Each of these preparations was subjected to phosphorylation with [$\gamma^{32}$P]ATP and Mg.$^{++}$, in the presence of added cAMP, with or without PKI. As seen in FIG. 2, panel A, no phosphorylation of p75 vitronectin occurred in platelet-free plasma alone. However, when platelet-containing plasma was stimulated with thrombin and the resulting white clot was spun down, p75 was subsequently phosphorylated in the supernatant and this phosphorylation was prevented by PKI (see FIG. 2, panel B). On the other hand, when intact, gel-filtered platelets were stimulated with thrombin, then spun down, and their supernatant subjected to endogenous phosphorylation under the same conditions, no evidence for the presence as p75 could be obtained (FIG. 2, panel C). Interestingly, though neither this supernatant alone nor the platelet-free plasma alone exhibited phosphorylation of p75, phosphorylation of p75 could be reproduced in the presence of added cAMP, and prevented by PKI (FIG. 2, panel D). Finally, the specific phosphorylation of p75 could be stimulated with pure catalytic subunit of PKA (from rabbit muscle (14)) added to platelet-free plasma (FIG. 2, panel E). As expected, also this phosphorylation was prevented by PKI.

EXAMPLE III

The specificity of plasma vitronectin phosphorylation by PKA is illustrated in tracing p75 during its purification, using the catalytic subunit of PKA as a reagent. When platelet-free plasma was subjected to ion exchange chromatography on DEAE-Sephadex with a linear salt gradient, most of the proteins were eluted between 0 and 250 mM NaCl. Upon raising the salt concentration with NaCl, a small protein peak emerged. Using the PKA assay mentioned above, this peak was shown to contain all of p75 (purification >50 fold). It should be noted that a very similar elution pattern was also obtained with human serum (sometimes with a minor $M_r$ 65000 band (p65)) even when the phosphorylation with PKA was carried out prior to chromatography, i.e., in the presence of all the other serum proteins.

EXAMPLE IV

Using antibodies against various human serum constituents, it was possible to immunochemically identify p75 as vitronectin (5) (also known as serum spreading factor or complement S protein). The p75 purified and [$\gamma^{32}$P]-labelled was quantitatively precipitated with goat antibodies against human vitronectin ($\alpha$V) but not with goat antibodies against human fibrinogen ($\alpha$F) or plasminogen ($\alpha$P) (FIG. 4). Vitronectin (p75 with a minor p65 band) also precipitated from whole serum with $\alpha$V (not shown).

The identification of p75 as vitronectin is also in agreement with its reported molecular weight, with its co-precipitation by $\gamma$V with p65 (possibly another biologically active form of p75) and with its behavior on ion exchange columns (6-8).

EXAMPLE V

Peptides containing the sequence Arg-Arg-Pro-X-Arg (X=Ser, Thr, Ala, Cys, Tyr) inhibit the phosphorylation of vitronectin by PKA. Apart from PKI (see FIGS. 1 and 2) a few other peptides were found to do so. For example, the octapeptide which had a sequence identical to that found at the site of phosphorylation of vitronectin (Ser 378), namely Ser-Arg-Arg-Pro-Ser-Arg-Ala-Thr, (X=Ser) was phosphorylated by PKA and thus competed with (inhibited) the phosphorylation of vitronectin (FIG. 5) with a Ki concentration of 30 $\mu$M.

EXAMPLE VI

The phosphorylation of vitronectin (p75 and mainly the p65 form) is affected by pH and by the presence of heparin in the reaction mixture (FIG. 6).

Legends to the Figures

FIG. 1 Lanes A to D: Aliquots of serum (5 $\mu$l) were diluted with buffer (40 $\mu$l) to yield a solution with the following final composition, Hepes (50 mM), Mg(CH$_3$COO)$_2$ (10 mM), cAMP (where added, 10$^{-5}$M), PKI (where added, 0.1 mg/ml), pH 7.5. Autophosphorylation was initiated by to the 45 $\mu$l sample of diluted serum 5 $\mu$l of [$\gamma^{32}$P]ATP (10 $\mu$M, 50 Ci/mmol). The reaction was allowed to proceed for 10 min at 30° C. and arrested by addition of 12 $\mu$l of a buffer solution containing sodium dodecylsulfate (10 %) and 2-mercaptoethanol (3.75 M), then boiled for 3 min at 95° C. Each of the reaction mixtures (at this stage 65 $\mu$l) was then subjected to gel electrophoresis (2.5 to 12 % linear gradient polyacrylamide) and autoradiography. Lane E: Phosphorylation of the same serum aliquot with pure catalytic subunit of PKA from rabbit muscle. Note that the low $M_r(<35$ kDa) bands seen in the autoradiogram are due to phosphorylatable bands in the PKI preparation used. These bands could be reproduced (lane E) by incubation of the same PKI preparation with the catalytic subunit of PKA and $[\gamma=P]ATP$. Lane F: Samples of the same sera (5 μl) were similarly electrophoresed and stained with 0.25 % Coomassie blue.

Figure 3:
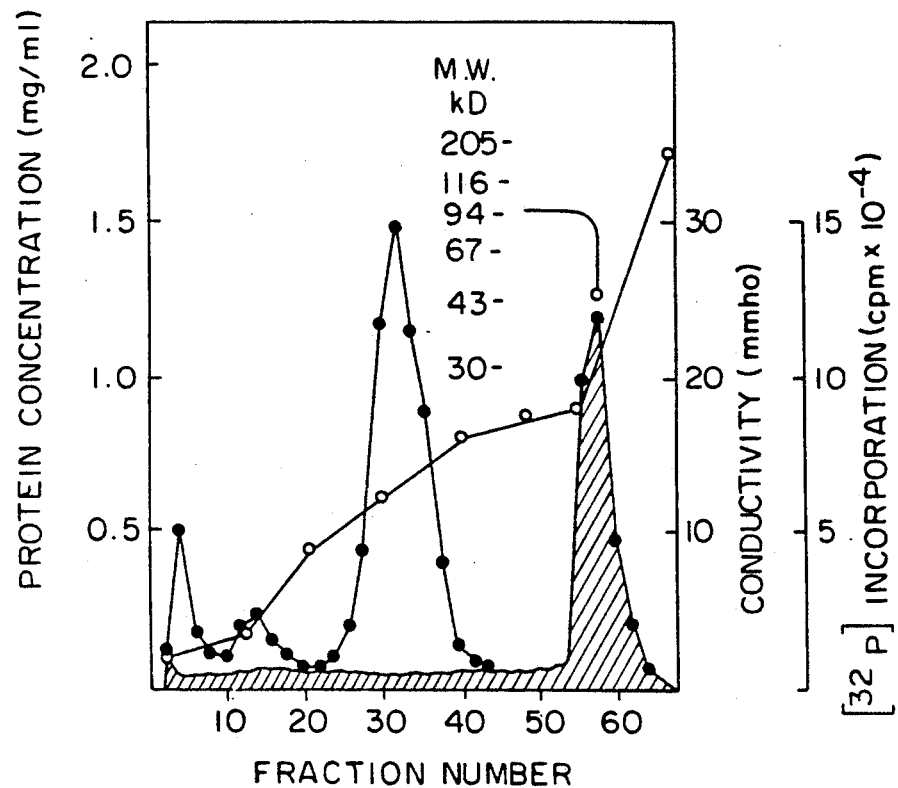
FIG. 3 is a graph plotting lines representing protein concentration, conductivity and $^{32}$P incorporation against human plasma fractions separated on a DEAE Sephadex column.

FIG. 2 Portions (45 ml) of fresh blood (obtained from volunteers as described in Example I) were withdrawn into polypropylene tubes containing 5 ml of trisodium citrate (3.8 % w/v). Protein phosphorylation was carried out in the presence of added cAMP (10.μM) and PKI (0.1 mg/ml), as indicated by the dots at the bottom of the figure. Analysis by gel electrophoresis (polyacrylamide 5-15 %), and autradiography were carried out as described previously (3). Panel A: platelet-free plasma (endogenous phosphorylation on samples of 5 μl). Panel B: Platelet-containing plasma (5 x 10a platelets/ml) stimulated with thrombin (1 U/ml). The suspension was incubated (30 min at 22° C.), centrifuged (10 min at 10000 rpm) and aliquots (5 μl) were assayed for endogenous phosphorylation. Panel C: Gel-filtered platelets stimulated with thrombin. A preparation of gel-filtered platelets (5×10a platelets/ml) was stimulated with thrombin (1 U/ml), incubated (30 min at 22° C.), centrifuged (10 min at 5000 rpm) and aliquots (20 μl) of the supernatant were assayed for endogenous phosphorylation. Panel D: Reconstitution of endogenous phosphorylation by combining the supernatant (20 μl) of thrombin stimulated platelets (C) with 5 μl of platelet-free plasma (A). The mixture was subjected to endogenous phosphorylation. Panel E: Simulation of the endogenous phosphorylation occurring in thrombin stimulated platelet containing plasma by addition of pure catalytic subunit of rabbit muscle PKA (final concentration 5 μg/ml) to platelet-free plasma (e). Samples of 5 μl were subjected to phosphorylation and analysis mg described in the legend to FIG. 1. For the low $M_r$ (<35000) band seen FIG. 3 A sample (250 μl) of human plasma was applied on a column (6.3×1 cm) of DEAE-Sephadex equilibrated and run (22° C.) with a buffer composed of 2-(N-morpholino)ethanesulfonic acid (5 mM), EDTA (1 mM) and NaCl (9 mM), pH 6.5. A linear NaCl gradient (9 to 250 mM NaCl in the equilibration buffer, total volume 50 ml) was applied, followed by a 10 ml final step of 500 mM NaCl in the same buffer. Fractions (1 ml) were collected and the following parameters were followed: protein concentration (°), conductivity ), [$\gamma^{32}P$] incorporation (o) The phosphorylation by PKA was assayed on aliquots (20 μl) of the indicated fractions. The reaction mixtures contained the following constituents at the indicated final concentrations: pure catalytic subunit of PKA from rabbit muscle (5 μg/ml), $Mg(CH_3COO)_2$ (10 mM), [$\gamma^{32}P$]ATP 10 μM, 50 Ci/mmole). Phosphorylation was allowed to proceed for 10 min at 30° C., arrested as described in the legend to FIG. 1, and subjected to gel electrophoresis (polyacrylamide 5-15 %) and autoradiography (inset). The lanes of the dry gels were cut out, and their radioactivity was counted in a scintillation counter using a toluene-based scintillent.

FIG. 4. Samples (20 μl) of the p75 peak fraction (number 58) in the experiment depicted in FIG. 3 were phosphorylated as described in the legend of that figure, bringing the total volume of the sample to 50 μl. Phosphorylation was arrested by addition of 25 μl of buffer I composed of NaF (150 mM), $Na_2P_2O_7$ (15 mM), EDTA (45 mM), $Na_3VO_4$ (6 mM), ATP (9 mM), Hepes (150 mM), pH 7.5. To each aliquot (75 μl) of the arrested reaction mixture, a suspension (5 μl) of Protein A Sepharose (50 % v/v in buffer I) was added (to remove any constituent that might react non-specifically with Protein A Sepharose). After an incubation of 15 min at 4° C., the samples were centrifuged (2 min at 12000 rpm), the supernatants were collected and incubated with 20 μl of one of the solutions of goat antibodies against vitronectin (αV), fibrinogen (αF) and plasminogen (αP) dissolved in buffer I diluted 1:3 (final concentrations 5 mg/ml). After an incubation of 3 h at 4° C. Protein A Sepharose (20 μl of 50 % v/v in buffer I) was added and the incubation was continued for an additional hour at 4° C. The samples were centrifuged (2 min at 12000 rpm) and the supernatants (marked S in the figure) were boiled (5 min at 98° C. in the presence of sodium dodecylsulfate (2 %) and 2-mercaptoethanol (0.15 M). The pellets (marked P in the figure) containing the immuno-complexes were washed twice with a solution composed of Hepes (50 mM), pH 7.5; Triton X-100 (1 % v/v); sodium dodecylsulfate (1 % w/v) and then once more with a solution composed of Hepes (50 mM), pH 7.5; Triton X-100 (1 % v/v); NaCl (150 mM). They were then dissolved by addition of 50 μl of a buffer solution containing sodium dodecylsulfate (2 % w/v) and 2-merceptoethenol (0.75 M) and boiled (5 min at 98° C.). The supernatants (S) and pellets (P) were subjected to polyacrylamide gel electrophoresis (polyacrylamide 5-15 and autoradiography.

Figure 5:
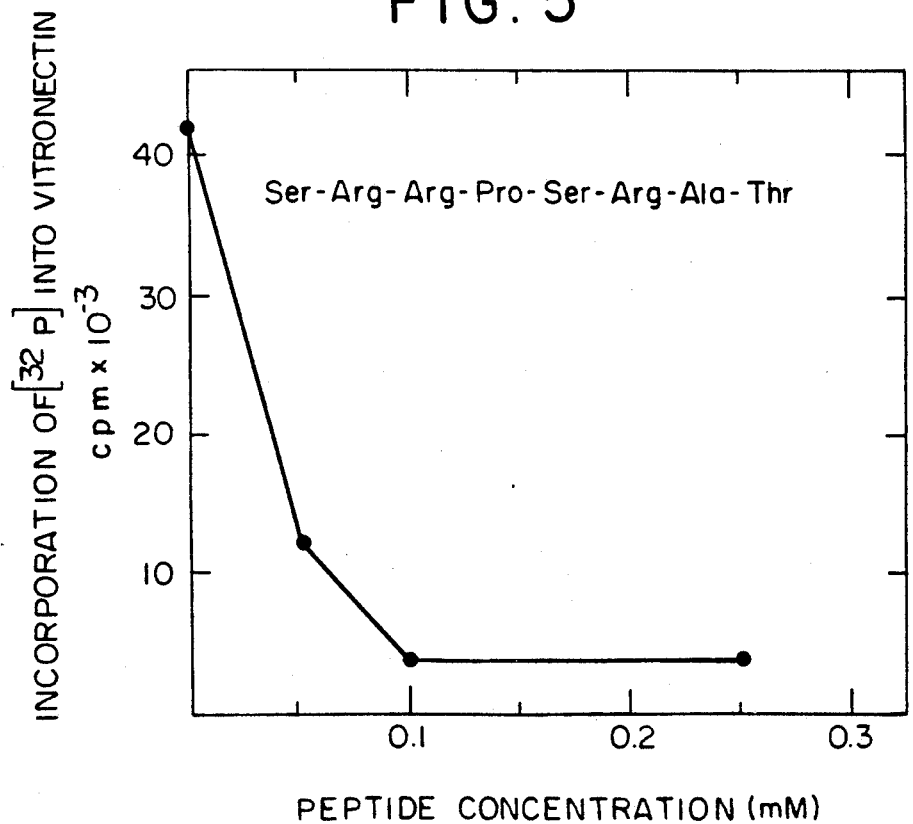
FIG. 5 is a graph plotting the degree of phosphorylation of vitronectin as a function of the amount of added peptide identical in sequence to the vitronectin phosphorylation site.

FIG. 5 Inhibition of vitronectin phosphorylation by PKA in the presence of the indicated concentrations of a peptide identical in sequence to the site phosphorylated in vitronectin.

FIG. 6 Vitronectin (2.7 μM was incubated for 2 h at 22° C. with C (1 μg/ml) in the presence of $Mg(CH_3COO)_2$ (10 mM), [$\gamma^{32}$]ATP 50 μM, 0.5 Ci/mmol), (50 Mes at the indicated pH), and a 3-fold molar excess of heparin over vitronectin (where indicated). The reaction was terminated by boiling in Laemli's sample buffer and the extent of phosphorylation was analyzed by polyacrylamide gel electrophoresis and autoradiography.

Bibliography

1. Walsh, D. A. et al., *J.Biol.Chem.*, 2433, 3763-3765, (1968).
2. Krebs, E. G., *The Enzymes*, XVII A, 3-20 (1986).
3. Korc-Grodzicki, B. et al., *Proc.Natl.Acad.Sci. U.S.A.*, 85, 7541-7545, (1988).
4. Holmsen, H., *Hemostasis and Thrombosis*, pp. 606-617 (Colman, R. W., Hirsh, J., Marder, V. J. and Salzman, E. W. eds.) 2nd edition, J. B. Lippincott Co. Philadelphia (1987).
5. Korc-Grodzicki, B. et al., *Biochem.Biophys.Res.Commum.*, 157, 1131-1138 (1988).
6. Barnes, D. W., Silnutzer, J., *J.Biol.Chem.*, 258, 12548-12552 (1983).
7. Suzuki, S., et al., *Proc.Natl.Acad.Sci. U.S.A.*, 83, 8614-8618 (1986).
8. Podack, E. R., Muller-Eberhard, H. J., *J.Biol.Chem.*, 254, 9908-9914, (1979).

9. Ill, C. R., Ruoslahti, E., *J.Biol.Chem.*. 260, 15610–15615, (1985).
10. Preissner, K. T., Müller-Berghaus, G., *J.Biol.Chem.*, 262, 12247–12253, (1987).
11. Jenne, D., Stanley, K. K., *EMBO J.*, 4, 3153–3157, (1985).
12. Hoffbrande A. V., Pettit, J. E., *Clinical Haemetology Illustrated*, pp13.2–14.12, Churchill, Livingstone, Edinburgh, London, New York (1987).
13. Walsh, D. A. et al., *J.Biol.Chem.*, 246. 1977–1985 (1971).
14. Beavo, J. A. et al., *Methods in Enzymol.*, 38C. 299–308 (1974).
15. Suzuki et al, *J.Biol.Chem.*, 259, 15307–15314 (1984).

What is claimed is:

1. A kit for assaying the cellular integrity of blood platelets which comprises a package, wherein said package contains PKA determining means for determining the quantity of PKA released by a number of platelets into a certain volume of plasma and wherein said PKA determining means comprises.
   (a) a tagged phosphate donor for use in determining cAMP-dependent phosphorylation of vitronectin; and
   (b) heparin, heparin-sulfate or another compound which is related to heparin and binds to the heparin-binding domain of vitronectin.

2. A kit for assaying the cellular integrity of blood platelets which comprises a package, wherein said package contains PKA determining means for determining the quantity of PKA released by a number of platelets into a certain volume of plasma and wherein said PKA determining means comprise:
   (a) at least one member selected from the group consisting of anti-PKA, anti-phosphovitronectin and anti-vitronectin antibodies; and
   (b) heparin, heparin-sulfate or another compound which is related to heparin and binds to the heparin-binding domain of vitronectin.

3. A kit for assaying the cellular integrity of blood platelets which comprises a package, wherein said package contains PKA determining means for determining the quantity of PKA released by a number of platelets into a certain volume of plasma and wherein said PKA determining means comprises:
   (a) a tagged phosphate donor for use in determining cAMP-dependent phosphorylation of vitronectin; and
   (b) a physiological platelet agonist which stimulates the release of PKA.

4. A kit for assaying the cellular integrity of blood platelets which comprises a package, wherein said package contains PKA determining means for determining the quantity of PKA released by a number of platelets into a certain volume of plasma and wherein said PKA determining means comprises:
   (a) at least one member selected from the group consisting of anti-PKA, anti-phosphovitronectin and antivitronectin antibodies; and
   (b) a physiological platelet agonist which stimulates the release PKA.

5. A kit in accordance with claim 1, wherein said PKA-determining means further comprises:
   (c) a physiological platelet agonist which stimulates the release of PKA.

6. A kit in accordance with claim 2, wherein said PKA-determining means further comprises:
   (c) a physiological platelet agonist which stimulates the release of PKA.

7. A kit for assaying the cellular integrity of blood platelets comprising a package containing:
   a container of a tagged phosphate donor capable of supplying phosphate in the cAMP-dependent phosphorylation of vitronectin;
   a container in which a phosphorylation reaction in a blood plasma sample can take place; and
   a container of heparin, heparin-sulfate or another compound which is related to heparin and binds to the heparin binding domain of vitronectin.

8. A kit for assaying the cellular integrity of blood platelets comprising a package containing:
   a container of a tagged phosphate donor capable of supplying phosphate in the cAMP-dependent phosphorylation of vitronectin;
   a container in which a phosphorylation reaction in a blood plasma sample can take place; and
   a container of a physiological platelet agonist which stimulates the release of PKA.

9. A kit in accordance with claim 7, wherein said tagged phosphate donor is ATP.

10. A kit in accordance with claim 8, wherein said tagged phosphate donor is ATP.

11. A kit for assaying the cellular integrity of blood platelets comprising a package containing:
    a container of a member selected from the group consisting of anti-IKA, anti-phosphovitronectin and antivitronectin antibodies;
    a container in which a phosphorylation reaction in a blood plasma sample can take place; and
    a container of heparin, heparin-sulfate or another compound which is related to heparin and binds to the heparin binding domain of vitronectin.

12. A kit for assaying the cellular integrity of blood platelets comprising a package containing:
    a container of a member selected from the group consisting of anti-PKA, anti-phosphovitronectin and antivitronectin antibodies;
    a container in which a phosphorylation reaction in a blood plasma sample can take place; and
    a container of a physiological platelet agonist which stimulates the release of PKA.

13. A kit in accordance with claim 1, further including instructions for use of the kit for assaying the cellular integrity of blood platelets.

14. A kit in accordance with claim 2, further including instructions for use of the kit for assaying the cellular integrity of blood platelets.

* * * * *